United States Patent [19]

Akkerman

[11] Patent Number: 5,681,857

[45] Date of Patent: Oct. 28, 1997

[54] ALKALINE SALT SOLUTIONS FOR TREATING CANCEROUS TUMORS

[75] Inventor: Boris D. Akkerman, Carlyle, Ill., Rimma Akkerman, executor

[73] Assignee: Estate of Boris D. Akkerman, Dallas, Tex.

[21] Appl. No.: 379,794

[22] Filed: Jan. 27, 1995

[51] Int. Cl.$^6$ ................................................ A61K 31/185
[52] U.S. Cl. ............................................................ 514/576
[58] Field of Search ............................................ 514/576

Primary Examiner—Allen J. Robinson
Attorney, Agent, or Firm—Patrick D. Kelly

[57] ABSTRACT

This invention discloses a new type of drug for treating cancer, comprising an alkaline salt that can reduce localized acidity levels in cancerous tumors. This drug comprises a water-soluble alkaline salt (such as a potassium salt) of a benzene ring having several pendant groups, including at least one acid group. One example comprises a vanillin derivative referred to herein as HMSBA, which is hydroxy-methoxy-sulfonic acid-benzyl alcohol. To prepare an alkaline salt solution for injection into the bloodstream of a cancer patient, a sufficient quantity of an alkali such as potassium hydroxide is added to a solution of HMSBA in water or saline buffer, until the pH of the mixture increases to about 7.3 to 7.4. A sufficient quantity of the aqueous solution is injected into the blood of a cancer patient to reduce the acidity of extracellular fluids in one or more cancerous neoplasms inside the body. When the acidity of such tumors is reduced from cancerous acidic levels to more physiologically normal levels, the patient's immune system can function more effectively to help fight and destroy cancer cells in the tumor. This treatment has been tested on humans as well as lab animals, and it has been shown to be very effective in reducing the size and severity of tumors. In a number of animals and people treated by this method, it resulted in apparently complete remission and cure.

6 Claims, 1 Drawing Sheet

VANILLIN

VANILLYL ALCOHOL

HMSBA

K - HMSBA

ALKALINE SALT SOLUTIONS FOR TREATING CANCEROUS TUMORS

BACKGROUND OF THE INVENTION

This invention is in the field of pharmacology, and relates to drugs that are useful for treating cancerous tumors.

The cellular physiology and genetic basis of cancerous tumors are well-known and are discussed in numerous reference works, including DeVita et al 1993, Calabresi and Schein 1993, and Holland et al 1993 (full citations to books and articles are provided below). However, despite billions of dollars worth of research into the causes of and potential treatments for cancer, there remains a need for improved pharmaceutical treatments, particularly for treatments which can improve and enhance the body's natural defense mechanisms.

It is known that most types of cancerous tumors generate localized areas of relatively high acidity (e.g., Harguindey 1982; Von Ardenne and Kruger 1979; Isaacs 1979). This acidity is believed to be due to a metabolic process known as "anaerobic glycolysis." In normal (aerobic) glycolysis, when sufficient oxygen is available inside a cell, molecules of glucose (a specific type of sugar molecule having 6 carbon atoms) are broken down all the way into carbon dioxide and water, in a series of reactions that generate a large quantity of energy to drive metabolic reactions. By contrast, anaerobic glycolysis occurs when not enough oxygen is present. The multi-step metabolic pathway of glycolysis is diverted at roughly the midpoint, and one of the major intermediates in glycolysis, pyruvic acid, is anaerobically converted into lactic acid instead of continuing down the aerobic pathway toward carbon dioxide and water. The accumulation of lactic acid at undesired levels generates a condition known as lactic acidosis, or simply acidosis.

When compared to normal tissue, cancerous tumors have a substantially higher tendency to divert their metabolic processes toward an undesired state of anaerobic glycolysis, because the unlimited rates of proliferation and cell division in cancerous tumors impose major demands on the oxygen being supplied to the cancerous tissue. Since so much oxygen is being diverted to reproduction of cancer cells, not enough is available to support fully aerobic glycolysis.

The pH of extra-cellular fluids in most types of normal and healthy tissue is slightly basic, with a pH of about 7.3 to 7.4. Although acute acidosis (to pH levels less than about 6 to 6.5, depending on the cell and tissue type) can cause cell death, most cells are able to survive indefinitely under conditions of mild acidosis, where pH levels do not drop below about 6.7, a pH level which often occurs in tissue surrounding cancerous tumors.

Another possibly important correlation between anaerobic glycolysis and cancer is supported by medical events and experiments in which a disruption of blood supply to a certain region of bone or soft tissue, caused by a bone breakage or tissue injury leading to contusion, led to the creation of a cancerous tumor at the affected location. There have been numerous reports of osteosarcomas (bone cancer tumors) arising at sites where bones had previously been broken in accidents, and where injuries that caused severe contusions in soft tissue were followed by the formation of cancerous tumors in the affected tissues. This is a controversial subject, and not everyone is convinced that a causal relationship exists; for a review of articles that argue both sides of this debate, see Gaeta 1993. Despite that debate, controlled experiments on cancerous lab animals have shown beyond any question that, "injured tissue appears to provide a better 'soil' for metastases, regardless of how the local tissue is damaged" (page 70 in Calabresi and Schein 1993).

Experiments carried out by the Applicant also add support to the assertion that a mechanical injury which causes ischemia (inadequate blood flow) and anaerobic glycolysis can cause or at least substantially increase the risk of cancerous tumors. In those experiments, the Applicant implanted a small plastic ring under the skin of lab animals. After several weeks, the ring was removed, and a relatively small circular growth was left behind. This growth was tied off, using a suture strand to encircle the base, creating a mushroom-shaped protrusion on the surface of the skin. The tight suture strand constricted blood supply to the tissue. Within several months, most of these growths with constricted blood supply usually turned cancerous.

These experiments, coupled with reports of cancer arising at areas where bones had been broken or where tissue had been subjected to mechanical trauma, suggest a direct and possibly causative correlation between locally inadequate blood flow, which leads to localized acidosis and elevated tissue acidity, and cancer formation.

In most cancer patients who are not at the end-stages of terminal cancer, the liver can readily eliminate the quantity of lactic acid generated by any tumors. Therefore, lactic acidosis which substantially reduces the pH of the entire blood circulation is relatively rare until the end-stages of terminal cancer, and most medical reports which correlate cancer and lactic acidosis involve systemic problems in acute or end-stage patients. Such problems are discussed under headings such as "Metabolic Emergencies" in Glover 1991 at page 325, and in DeVita et al 1993 at page 2137. In end-stage patients suffering from severe acidosis, sodium bicarbonate is sometimes administered orally or by injection, in an effort to directly reduce the acidity. However, several reports have stated that administration of sodium bicarbonate is actually counterproductive, since it can increase lactate and carbon dioxide production and impair oxygen delivery without improving survival rates (Cooper et al 1990, Stacpoole 1986, and Ritter et al 1990).

The reports which discuss systemic lactic acidosis in critically ill cancer patients do not focus upon what may be causative or vicious-circle interactions, in which acidosis, rather than being merely a side-effect of cancer, may help create or aggravate the growth of cancer, and may increase the likelihood of formation of metastatic tumors at sites other than the site of the original tumor.

Although it apparently has not been widely reported or appreciated, one result of the increased acidity in cancerous tumors appears to be the following: the body's immune system tends to function less effectively in localized areas of elevated acidity. This is due, at least in part, to the fact that most types of "affinity" binding become weaker as acidity increases. Affinity binding includes the molecular binding reactions between antibodies and antigens, and the cellular binding reactions between white blood cells and invader cells that the white blood cells are attacking. These attractions and binding reactions become weaker as acidity increases, because increasing concentrations of free, positively-charged hydrogen ions interfere with and disrupt the positive-negative attractions that are the basis of affinity binding. Antibodies and phagocytes cannot work as effectively in tissue having increased acidity.

It should also be noted that cancer cells tend to have thinner cell membranes than normal, healthy cells. This factor has been the foundation of numerous types of chemoand radiation therapy, which use the general principle that cancer cells tend to be more susceptible to death due to cell stress and damage than normal cells. Without criticizing that approach, it appears that few, if any, researchers have previously found a way to take advantage of a very different metabolic distinction between cancer cells and healthy cells: the fact that cancerous tumors tend to undergo anaerobic glycolysis and generate more acidity than healthy cells. This invention, rather than inflicting serious damage on all cells in an effort to preferentially kill cancer cells, offers a more benign approach to treating cancer.

Accordingly, one object of this invention is to disclose a pharmaceutically acceptable and non-toxic drug which can be administered to a human patient or other mammal suffering from cancer, to reduce the localized acidity levels in cancerous tumors. When the localized acidity in a tumor is decreased, the body's natural defense mechanisms can function more effectively to help fight and destroy the cancer cells.

Another object of this invention is to disclose a method of reducing the localized acidity levels in cancerous tumors in a mammalian patient, using a pharmaceutically acceptable and non-toxic drug.

Another object of this invention is to disclose a treatment which can help prevent or treat metastatic tumors at sites other than a primary tumor site.

Another object of this invention is to disclose a treatment which can function effectively as a stand-alone treatment, in some situations, and which can also serve as an adjunct to accompany other forms of cancer treatment, such as surgery, radiation, or chemotherapy.

These and other objects of the invention will become clear through the following summary and description.

SUMMARY OF THE INVENTION

This invention discloses a new type of pharmaceutically acceptable and non-toxic drug for treating cancerous tumors (neoplasms). This drug comprises an alkaline salt that can be administered to a human or other mammalian patient or lab animal suffering from cancer, to reduce the localized acidity levels in cancerous tumors in the patient's body. This drug comprises a pharmaceutically acceptable alkaline salt (such as a potassium salt of an acidified vanillin derivative) in a solution having a slightly basic pH such as about 7.3 to 7.4. This alkaline salt is prepared from an acid having a benzene ring with several pendant groups, as follows:

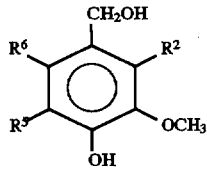

wherein at least one of R2, R5, or R6 comprises an acidic moiety which renders the compound highly soluble in water, such as a sulfonic acid group, $HOSO_2$. There are several chemically acceptable names for the sulfonated compound, including 4-hydroxy-3-methoxy-[X]-sulfonic acid benzyl alcohol, where X is 2, 5, or 6, depending on which carbon atom the sulfonic acid group is attached to. This compound, referred to herein as HMSBA, can be synthesized from any of several starting compounds, such as vanillin or vanillyl alcohol.

To prepare an alkaline salt solution for injection into the blood circulation of a cancer patient, a sufficient quantity of a suitable alkali, such as potassium hydroxide, is added to a solution of the HMSBA acid in water or saline buffer, until the pH of the mixture increases to an alkaline level, such as about 7.3 to 7.5. The solution preferably should be isotonic with human blood. A sufficient quantity of the mixture is then administered to a patient suffering from cancer, by periodic injection or continuous intravenous infusion, to reduce the acidity of extracellular fluids in the patient's body. When the acidity of a tumor is reduced from an acidic level to a more physiologically normal level, the patient's natural immune system can function more effectively to help fight and destroy cancer cells in the tumor. This treatment can be used on a stand-alone basis, or as an adjunct to accompany surgery, chemotherapy, or radiation therapy. This alkaline salt treatment has been tested on humans as well as lab animals, and it has been shown to be very effective in reducing the size and severity of tumors. In a number of animals and people treated by this method, it resulted in apparently complete remission and cure.

DESCRIPTION OF THE PREFERRED EMBODIMENTS

This invention discloses a new method of using alkaline salt solutions which meet certain biochemical and physiological requirements, to treat human patients or other mammals suffering from cancer. This alkaline salt treatment has been tested on humans as well as lab animals, and it has been shown to be effective in reducing the size and severity of tumors. In a number of animals and people that were treated by this method, it resulted in apparently complete remission and cure.

Although a molecular theory of why this treatment works is not necessary to enable practical and effective use of this method, it is believed that this treatment reduces the localized acidity levels of extracellular fluids in cancerous tumors in the patient's body. When the acidity of a cancerous tumor is reduced from an acidic level to a more physiologically normal level, the patient's natural immune system (including antibodies, macrophage cells, etc.) can function more effectively to help fight and destroy cancer cells in the tumor.

It should also be noted that a large number of cancer deaths are due to secondary infections, usually by bacteria. If a patient's immune system is suppressed by acidosis, either bacterial-induced or tumor-generated, then the treatment described herein may be able to boost the systemic functioning of the immune system, thereby helping the patient fight off secondary infections as well as helping the immune system fight the cancer.

Figure 1:
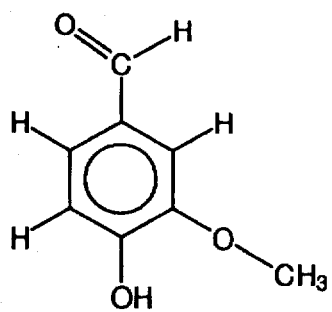
FIG. 1 depicts the chemical synthesis steps that were used to create an alkaline salt solution as described herein, using vanillin as a starting compound.
Figure 1:
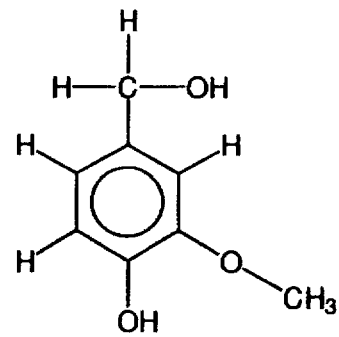
Figure 1:
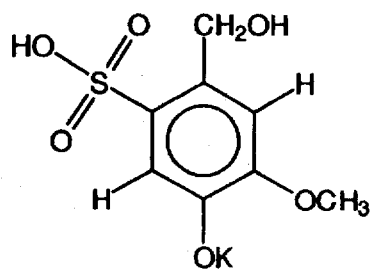
Figure 1:
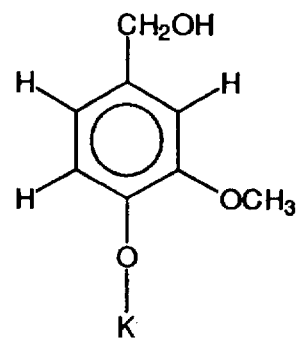
Figure 1:
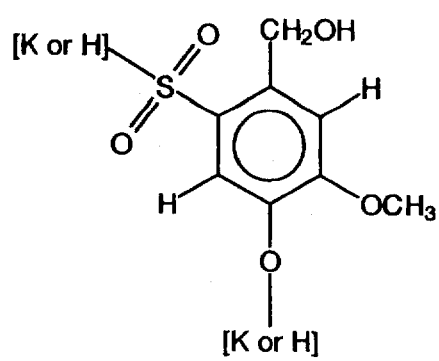

One form of alkaline salt solution which was synthesized and used in a number of animals and humans suffering from cancer, with excellent results, comprises a potassium salt formed from HMSBA which was synthesized from vanillin, a benzene derivative with three pendant moieties, shown as the starting compound in FIG. 1. Other starting compounds, such as vanillyl alcohol or protocatechuic acid, could alternately be used to create the same final compound. Synthesis using 4-hydroxy-3-methoxybenzyl alcohol (also called vanillyl alcohol; compound 2 in FIG. 1) as the starting material would eliminate the first reaction shown in FIG. 1. Vanillyl alcohol having this configuration is commercially available from Aldrich Chemical Company, Milwaukee, Wis. (catalog number 17,553-6).

One series of reactions which can be used to create a potassium salt of HMSBA, referred to herein as K-HMSBA, is described in more detail in Example 1. The first step, a hydrogenation reaction, converted the aldehyde group on the #1 carbon atom of vanillin to an alcohol group, to create 4-hydroxy-3-methoxybenzyl alcohol (also called vanillyl alcohol; compound 2 in FIG. 1). The second reaction added potassium hydroxide at room temperature until the pH of the solution was 7.4; this converted the hydroxyl group on the #4 carbon atom to potassium oxide. The third step involved chilling the mixture in an ice bath and slowly adding concentrated sulfuric acid with vigorous stirring. This caused sulfonic groups to displace one or more of the hydrogen atoms attached to the #2, #5, or #6 carbon atoms on the vanillin ring. As discussed below, due to weakening of hydrogen bonds at the two ortho positions (the #2 and #6 carbon atoms) by the alcohol group at the #1 carbon atom, it is believed likely that sulfonic groups will be added preferentially at either of the ortho positions, rather than at the meta position at the #5 carbon atom. If further research shows that the position of the sulfonic group is crucial to therapeutic use of the salt against cancer as described herein, various techniques known to synthetic chemists can be used to accomplish those goals.

It should be noted that vanillin is only about 2% (weight per volume) soluble in water; it forms a solid white precipitate if present at higher concentrations. Vanillyl alcohol is not much more soluble than that, and remained as a white precipitate after the hydrogenation reaction 2 shown in FIG. 1. However, sulfonation of the vanillyl alcohol intermediate caused a major increase in its solubility.

In aqueous solutions, the salts described herein will establish an equilibrium between the salt form and the acidic form. The sulfonic moiety will alternate back and forth, in equilibrium, between the hydrogen (acid) form and the potassium salt form, as follows:

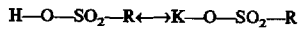
H—O—SO$_2$—R←→K—O—SO$_2$—R where R represents the benzene ring and the other pendant moieties. The quantity of hydrogen versus potassium atoms on the sulfonic moiety when the mixture is in equilibrium will depend upon the pH of the mixture and the concentration of potassium ions in the solution. Both of these can be controlled directly and easily, by adding controlled amounts of KOH (potassium hydroxide, also called potash, which is highly alkaline) to the mixture.

A hydroxyl group attached to a benzene ring tends to be acidic, which allows hydrogen ions to dissociate from the hydroxyl group. Therefore, the hydroxyl moiety at the #4 carbon atom of the benzene ring will also establish an acid-salt equilibrium with potassium ions, as follows:

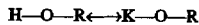
H—O—R←→K—O—R

A preferred buffer salt for use in the aqueous mixtures described herein comprises potassium phosphate, which will establish equilibrium between two species, as follows:

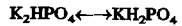
K$_2$HPO$_4$←→KH$_2$PO$_4$

In general, potassium salts are preferred over sodium salts for use via intravenous infusion to treat cancer patients as described herein, because substantial quantities of salt may need to be infused into a patient over a continuous period such as several days in a row. Infusion of a large quantity of sodium can severely disrupt various biochemical balances in the body, while infusion of similar quantities of potassium tends to be less disruptive and harmful. Alternately, to minimize the quantity of either ion that must be intravenously infused into a patient, a mixture of both sodium salts and potassium salts can be used. In addition, the sodium salt might be preferred for patients suffering from hyponatremia (i.e., abnormally low sodium levels in the blood, which can be caused by cancer-induced disruptions of various hormones).

Additionally or alternately, other salts might be used, including various organic or metallic salts, if they meet the following requirements: (1) they must be pharmaceutically acceptable and have an acceptably low level of toxicity; (2) they must have sufficiently high levels of solubility in water or a buffered saline solution; (3) they must allow the salt to be infused into the patient in a stable and slightly alkaline solution having a pH value of about 7.2 to about 7.5, in water or a buffered saline solution; and, (4) they must have sufficiently high levels of cationic (alkaline) dissociation to allow the remaining negatively charged molecules to effectively reduce the acidity of intracellular fluids.

Analogs and Derivatives; Placement of the Pendant Groups

Due to weakening of the hydrogen bonds at the two ortho positions (at the #2 and #6 carbon atoms) by the alcohol group at the #1 carbon atom, it is believed likely that sulfonic groups may be added preferentially at either of the ortho positions, rather than at the open meta position (at the #5 carbon atom). If further research shows that the position of the sulfonic group is crucial to therapeutic use of the salt against cancer as described herein, or if it is found to be necessary to attach only one sulfonic group per vanillin molecule, various techniques known to synthetic chemists can be used to accomplish those goals.

In addition, because the quantity of sulfuric acid added to the solution was limited, it is believed that the majority of HMSBA molecules created and tested by the Applicant contained only one sulfonic acid moiety per molecule. By adding a larger molar ratio of sulfuric acid, it may be possible to create vanillin derivatives that contain two or even three sulfonic acid groups. Such bisulfonate or trisulfonate compounds can be created and tested in alkaline salt solutions for pharmaceutical acceptability, non-toxicity, and anti-cancer efficacy as described herein, using no more than routine experimentation.

Since this compound is believed to work via chemical mechanisms involving acidity, alkalinity, and solubility in water, rather than interactions with enzymes that interact only with substrates having certain spatial arrangements, it is not believed to be critical to this invention that the various moieties attached to the benzene ring must be attached to particular carbon atoms to provide the exact configuration shown in FIG. 1. The arrangement of groups attached to the benzene ring of HMSBA shown FIG. 1 was controlled by the arrangement of the pendant groups on vanillin, the starting compound used to create the test compound described herein. By using different starting reagents comprising benzene rings with pendant groups at different positions, or by using other synthetic techniques known to chemists, alternate molecules having the same groups attached to the benzene ring at different locations can be created and tested in alkaline salt solutions for pharmaceutical acceptability, non-toxicity, and anti-cancer efficacy. Such synthesis and testing will require only routine experimentation.

Similarly, various other analogs and derivatives can also be created and tested using no more than routine experimentation. For example, the methyl alcohol group attached to the #1 carbon atom on the compound shown in FIG. 1 can be replaced by an ethanol, propanol, isopropanol, or other alcohol moiety. Similarly, the methoxy group on carbon #3 can be replaced by an ethyoxy or propyloxy group, or any other alkyl group coupled to the benzene ring through an ether linkage. Similarly, compounds having ester groups rather than the methoxy group of HMSBA, and compounds having other types of acid groups (such as carboxylic acid groups) rather than the sulfonic acid group of HMSBA, can be created and screened. Any of these analogs can be created, converted into an alkaline salt solution, and tested for pharmaceutical acceptability, non-toxicity, and anti-cancer efficacy as described herein, using no more than routine experimentation.

Accordingly, this invention covers a method of treating cancer, using an alkaline salt solution formed by reacting an alkaline compound with an acid have the following formula:

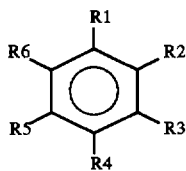

wherein at least one of R1 through R6 comprises an alkyl alcohol group, and wherein at least one of R1 through R6 comprises a hydroxyl group, and wherein at least one of R1 through R6 comprises an alkyl group coupled to the benzene ring through an ether or ester linkage, and wherein at least one of R1 through R6 comprises a sulfonic acid group.

In a broader sense, this invention discloses a method of treating cancer, using an alkaline salt solution prepared from a water-soluble, pharmaceutically acceptable organic acid. Although a benzene ring was chosen for the first reduction to practice, due to the stability of benzene rings and the relative ease of working with pendant groups attached to benzene rings, it is not essential that an organic acid utilize a benzene ring as its foundation to be useful for treating cancer as described. Comparable pendant groups which increase the solubility of an organic compound in water can be coupled to straight chain organic molecules (either saturated or unsaturated), to cyclic organic rings such as cyclopentane or cyclohexane, or to heterocyclic rings such as pyridine, pyrrole, oxane, or furan rings. In addition, the method of using an alkaline salt solution to reduce the pH of tumors might also be combined with other forms of chemotherapy, by using an alkaline salt solution prepared from a drug which is therapeutically useful against cancer cells due to some other, independent molecular mechanism.

In order to be useful for anti-cancer use as described herein, a combination of moieties attached to a benzene ring or other organic molecule as described herein must provide a compound which is soluble in water or in a pharmaceutically acceptable buffered saline solution, such as a phosphate-buffered saline (PBS). Numerous types of suitable buffers are available, including buffers which also contain glucose or other sugars, such as Ringer's lactate solution. The compound, in its alkaline salt form in a suitable aqueous buffer at the quantities and concentrations used must be effective for reducing the acidity of extracellular fluids in the tumorous tissue, to render it suitable for use according to this invention.

The terms "analogs" and "derivatives" are used in a conventional chemical sense. In general, an analog of the compound shown in FIG. 1 is a molecule which resembles the molecule of FIG. 1, but which has been modified by substituting or altering one or more chemical groups on the referent compound. A derivative of the compound shown in FIG. 1 refers to a molecule which is created by chemically treating the compound shown in FIG. 1. This invention anticipates that various analogs and derivatives of the compound shown in FIG. 1 will be synthesized and screened for anti-cancer activity, using the procedures described herein or various routine procedures known to those skilled in the art. If such analogs or derivatives prove to be more effective than the specific salts discussed herein for fighting cancer, they may rise to the level of patentable improvements; however, if they arise directly from the disclosures herein and are analogs or derivatives of the compounds described herein, they are within the scope of the subject invention.

Modes of Administration

The alkaline salt solutions of this invention can be administered directly to the bloodstream, by means such as periodic injections, intravenous infusion, use of an implanted osmotic mini-pump or other slow-release device, etc. As used herein, the term "injection" includes any such method of introducing the compound directly into the blood circulation, without requiring passage through the digestive system.

Although intramuscular injection might be suitable in some cases, it is not preferred, since it might lead to or aggravate tissue reactions and cause soreness due to the relatively large volumes that will be injected.

Injectable formulations preferably should be isotonic with blood, and should have a pH of at least about 7.2, and preferably about 7.35 to 7.4. Concentrations anticipated herein range from about 0.002 to about 0.1 molar. If desired, a relatively dilute solution can be tested initially on a patient to ensure that it does not cause an allergic or other adverse reaction, and the concentration can be increased if no adverse side effects are encountered.

The alkaline salts described herein can also be administered orally if desired, such as in liquid form, in a tablet or capsule, or as a food additive. If oral administration is used, the dosage should be in the range of about 100 to about 2000 mg/day, depending on the body weight and medical condition of the patient.

If a solidified, crystalline formulation of an acid or salt described herein is desired for purposes such as shipping and storage or oral administration, it can be prepared by conventional methods, such as lyophilizing (i.e., freeze-drying under a vacuum) an aqueous solution containing the acid or salt.

Regardless of the mode of administration, the patient's blood pH should be monitored during the treatment, and the dosage should be adjusted to accommodate the needs of the patient, in light of the fact that one of the primary objectives of this invention is to restore the alkalinity of the blood in the tumor to near-physiological levels of about 7.37. Whenever possible, the pH of the fluid inside a tumor, or the pH of blood emerging from a tumor, should be monitored in the most direct manner practicable, by means such as inserting a hypodermic needle into a vein that carries blood away from the tumor, or by inserting the tip of a pH-monitoring electrode directly into a tumor.

The terms "cancer" and "tumor," as used herein, refer to cellular growths usually referred to as "neoplasms" by doctors. It is not claimed that the alkaline salts disclosed herein will effectively treat every form of cancer; instead, what is taught herein is a compound and method which has been shown to be useful and effective in treating at least some forms of cancer. Through routine testing, doctors will be able to determine which forms of cancer can be treated most effectively by the compound and method disclosed herein, and the optimal timing of such treatments in relation to other treatments such as surgery, radiation, and chemotherapy. It should be noted that in tests on mice and in several human experiments, administration of K-HMSBA for several weeks prior to surgery led to formation of what appeared to encapsulating membranes that surrounded the tumors. This made it easier to remove the tumors as discrete lumps of tissue, and appeared to minimize surgical trauma on the surrounding tissue.

As used herein, the term "therapeutically useful" refers to a treatment which helps a patient's body fight or resist cancer, regardless of the specific molecular mode of action of the alkaline salts disclosed herein, and regardless of whether a cancer in a specific patient goes completely into remission. For example, a treatment which prolongs survival or helps ameliorate pain is useful, even if it cannot provide complete remission in a specific patient.

EXAMPLES

Example 1

Synthesis of K-HMSBA

Vanillin, a white solid with low solubility in water, was hydrogenated by stirring it in water while bubbling hydrogen gas up through the water at room temperature in a conventional hydrogenation vessel, using nickel as a catalyst. This reaction converted the aldehyde group on the #1 carbon atom of vanillin to an alcohol group, creating 4-hydroxy-3-methoxybenzyl alcohol (vanillyl alcohol), shown as compound 2 in FIG. 1.

The second reaction added potassium hydroxide at room temperature until the pH of the solution was 7.4; this converted the hydroxyl group on the #4 carbon atom to potassium oxide. This compound also had relatively low solubility in water.

The third reaction involved chilling the mixture in an ice bath and slowly adding concentrated sulfuric acid while the mixture was being vigorously stirred. This caused one or more of the hydrogen atoms attached to the #2, #5, or #6 carbon atoms on the vanillin ring to combine with a hydroxyl group on a sulfuric acid molecule, thereby adding one or more sulfonic acid groups to one or more of the #2, #5, or #6 carbon atoms. This created 4-hydroxy-3-methoxy-[X]-sulfonic acid benzyl alcohol, where X is 2, 5, or 6, depending on which carbon atom the sulfonic acid group is attached to. This compound (or mixture of compounds) was highly soluble in water.

To create an alkaline salt solution, potassium hydroxide was added dropwise at room temperature until the pH of the mixture increased to about 7.35.

Example 2

Bacterial Tests on the Effects of Acidity on the Defensive Activity of White Blood Cells A series of cell culture tests were carried out to assess the effects of acidity on the defensive activity of leukocytes (white blood cells). These tests used *Coli commune* bacteria, which are rod-shaped gram-negative bacteria often found in contaminated milk, which readily convert glucose into several types of acid, including lactic acid.

In these tests, 4 ml of blood was diluted 4:1 by adding 16 ml of a 2% w/v glucose solution in water. In a small tube, 1 ml of diluted blood solution was mixed with 0.4 ml of a bacterial solution containing $10^4$ cells/ml. After half an hour, and every half hour thereafter for several hours, the pH of the blood and bacteria mixture was tested, and a small drop of the mixture was removed, placed on a glass microscope slide, and visually examined under a light microscope. In normal blood, which has a pH of about 7.3, phagocytosis of the bacterial cells by phagocytes (which are certain types of leukocytes) can be readily observed; the phagocytes can be seen surrounding, enveloping, and digesting the smaller bacterial cells.

Over a period of several hours, the pH of the blood-bacteria solution dropped, as bacteria that had not yet been killed by the phagocytes continued to proliferate and convert glucose into acid. As the pH dropped, the activity of the phagocytes decreased, as could be seen through visual observation under the microscope. By the time the pH of the solution dropped to below 6.9, phagocytic activity had dropped sharply; most phagocytes stopped binding to or engulfing the bacterial cells. By the time the pH of the solution dropped to about 6.7, phagocytic activity had completely ceased.

This experiment showed that the defensive activities of phagocyte cells against invader cells is pH dependent, and decreases as pH decreases from physiologically normal levels of about 7.3, to levels such as about 6.9 or lower, as often occurs in tumors and other tissue suffering from acidosis.

Example 3

Mouse Experiments

Three different mouse lines were used, each a preferred host for a certain type of cancerous tumor. Female mice about 6–7 weeks old were used. A control group was not inoculated with cancer. The inoculation groups had 34 mice in each group. Group MS was inoculated with cells from a mouse melanosarcoma known as B-16 melanosarcoma. Group HEP was inoculated with cells from a mouse liver cancer known as MN-134 hepatoma. Group PUL was inoculated with cells from a mouse lung cancer known as Lewis pulmonary carcinoma. All mice were inoculated with cancer cells mixed with an oil emulsion which aided binding of the cancer cells to cellular or skeletal surfaces inside the mice.

Each cancer-inoculated group (MS, HEP, and PUL) was divided into 3 treatment groups having 4 mice in each, and a control group of 8 mice which received no treatment for 3 months; after three months, when their tumors were fairly advanced, these control mice were used in a different experiment, described in Example 4.

For each line of cancer cells, each of the four treatment groups were treated using a 15% (by weight) solution of HMSBA, synthesized using the steps shown in FIG. 1 with vanillin as a starting reagent, which had been converted to the potassium salt (K-HMSBA) by adding KOH until the pH was 7.35. Injections were made three times daily (morning, noon, and late afternoon) using 1 ml of solution for each injection. An effort was made to inject the solution intravenously, directly into the tail vein; however, it was sometimes difficult to ensure that a vein was pierced by a hypodermic needle, and some of the injections were merely subcutaneous. The treatments for each different type of cancer line were as follows:

Group MS-1, HEP-1, or PUL-1: injected with K salt on day 1 after cancer cell inoculation Group MS-8, HEP-8, or PUL-8: injected with K salt on day 8 after cancer cell inoculation Group MS-28, HEP-28, or PUL-28: injected with K salt on day 28 after cancer cell inoculation All of these treatment groups also received 0.8 to 1.0 g of the K-HMSBA salt in their drinking water, twice every 24 hours. The mice were housed four in each cage, with all four animals in a cage receiving identical treatments.

Most mice can survive for longer than 8 months with the types of tumors that used herein. However, some of the mice died of causes other than cancer during the course of the tests. Several of these deaths followed injections that were probably made improperly and may have been subcutaneous rather than intravenous; other deaths were from spurious causes such as unidentified infections. In Table 1, the values for "# surviving" reflect these deaths from non-cancer causes.

The test ended after 8 months; at that time, all surviving animals were sacrificed, dissected, and examined. The results are provided in Table 1.

TABLE 1

RESULTS OF MOUSE TESTS

| Treatment Group | # surviving | Tumor evidence |
|---|---|---|
| MS-1 | 4/4 | None |
| MS-8 | 3/4 | None |
| MS-28 | 4/4 | 2 mice: small tumors |
| MS controls | 6/8 | see Example 4 |
| HEP-1 | 4/4 | None |
| HEP-8 | 4/4 | None |
| HEP-28 | 3/4 | 1 mouse, suspected tumor |
| HEP controls | 8/8 | see Example 4 |
| PUL-1 | 4/4 | None |
| PUL-8 | 4/4 | None |
| PUL-28 | 2/4 | 1 mouse, suspected tumor |
| PUL controls | 6/8 | see Example 4 |

Example 4

Additional Tests on Control Mice

After 3 months, an additional experiment was commenced on the control groups. This group initially included 24 mice that had been inoculated with cancer cells and did not receive any of the potassium salt. Four of these mice had died within the 3 month period, of causes other than cancer. The remaining 20 control mice were divided into 2 groups of 10 mice each. One group was treated as described in Example 3, receiving K-HMSBA twice daily in their drinking water and three 1 ml injections on the first day of the fourth month. After eight months, 8 of the ten mice in the K-HMSBA-treated group survived, while only 5 of the ten mice that did not receive K-HMSBA survived. All of the control mice were dissected, either at the time of death, or at the end of the experiment at 8 months after inoculation. The ten mice in the "true" control group (completely untreated) all had large, easily visible tumors. The eight mice which survived the entire 8 months in the delayed treatment group had tumors that were substantially smaller than the true controls, and their tumors also appeared to be encapsulated within a membrane-like fibrous layer. These encapsulated tumors could be easily removed from the surrounding tissue.

Example 5

Tests on Human Patients

Experimental tests on about 10 human cancer patients were carried out. These were all performed a number of years ago in the former Soviet Union.

These patients received an intravenous injection of 0.005 molar solution of K-HMSBA in saline solution buffered with potassium phosphate, pH 7.3 to 7.4, three times per day at 150 ml/session, for 3 successive days followed by a 4 day rest period. This regimen was repeated several times, depending on the stage of the cancer. Each patient also had fresh blood transfusions three times per month, 125 ml per transfusion.

Several patients who were tested with full approval from the Soviet government suffered from advanced terminal cancer, in which organ destruction was already extensive. Since these patients were in an apparently hopeless stage with death imminent, the Soviet government approved an experimental treatment on them. Due to the advanced stage of their disease, none of those patients survived more than a few days or weeks after treatment.

A number of other cancer patients were discretely nominated by physicians or surgeons who had heard of the results of the mouse tests using K-HMSBA. Most of those patients were relatives of the doctors who nominated them for the experimental treatment.

Six of these patients had tumor removal surgery after two months of K-HMSBA treatment, and the K-HMSBA treatment continued for several months after the surgery. To the best of the Applicant's knowledge, all six of those patients survived for at least 10 years after the treatment, apparently in complete remission.

Two of the other patients nominated by doctors received the experimental treatment but no surgery. Both of those patients survived for more than 5 years after treatment, apparently in complete remission. The Applicant lost contact with them after five years.

Thus, with the very positive results shown in both lab animal and human tests, there has been shown and described a new and useful compound and method for treating neoplasms in patients suffering from cancer. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Calabresi, P. and Schein, P. S., *Medical Oncology*, 2nd edition (McGraw Hill, New York, 1993)

Cooper, D. J., et al, "Bicarbonate does not improve hemodynamics in critically ill patients who have lactic acidosis," *Annals Internal Med.* 112: 492–498 (1990)

Devita, V. T., et al, *Cancer: The Principles and Practice of Oncology*, 4th edition (Lippincott, Philadelphia, 1993)

Holland, J. F., et al, *Cancer Medicine*, 3rd edition (Lea & Febiger, Philadelphia, 1993)

Ritter, J. M., et al, "Paradoxical effect of bicarbonate on cytoplasmic pH," *Lancet* 335: 1243–1246 (1990)

Stacpoole, P. W., "Lactic acidosis: The case against bicarbonate therapy," *Annals Internal Med.* 105: 276–279 (1986)

Gaeta, J. F., "Trauma and inflammation," pp. 261–264 in Holland 1993

Glover, D., "Metabolic emergencies," pp 320–327 in R. E. Wittes, *Manual of Oncologic Therapeutics* (Lippincott, Philadelphia, 1991)

Harguindey, S., "Hydrogen ion dynamics and cancer: an appraisal," *Med. Pediatr. Oncol.* 10:217–36 (1982)

Isaacs, M., "Life-threatening fluid and electrolyte abnormalities in patients with cancer," *Curr. Probl. Cancer* 4: 6–14 (1979)

Von Ardenne, M., and Kruger, W., "Local tissue hyperacidification and lysosomes," *Frontiers Biol.* 48: 161–94 (1979)

It is claimed:

1. A method of treating a mammalian patient suffering from a cancerous neoplasm, comprising the step of administering to the patient a water-soluble alkaline salt of an acid which is selected from the group consisting of:

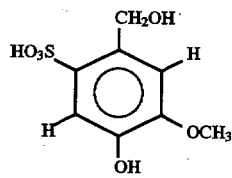

and salts and isomers thereof, wherein the alkaline salt, when dissolved in a suitable aqueous carrier liquid, is pharmaceutically acceptable and therapeutically useful, when administered in a therapeutically effective quantity, in treating cancerous neoplasms which are susceptible to such treatment.

2. The method of claim 1 wherein the alkaline salt is administered by injecting, into a patient's blood circulation, an aqueous solution containing the alkaline salt and having a pH in the range of about 7.2 to about 7.4.

3. The method of claim 1 wherein the alkaline salt comprises a potassium salt.

4. A composition of matter, comprising an acid which is water-soluble and which has a molecular structure selected from the group consisting of:

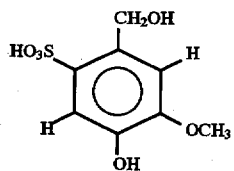

and salts and isomers thereof, wherein the acid can be mixed with a suitable aqueous carrier liquid to create an aqueous mixture which can be converted, by means of adding a suitable alkaline compound to the aqueous mixture, into an alkaline salt solution which is pharmaceutically acceptable and therapeutically useful, when administered in a therapeutically effective quantity, in treating cancerous neoplasms which are susceptible to such treatment.

5. A composition of matter comprising a mixture of (a) an aqueous carrier solution which is pharmaceutically acceptable when injected into a mammalian patient, and (b) an acid which is water-soluble and which has a molecular structure selected from the group consisting of:

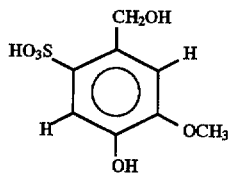

and salts and isomers thereof, wherein the mixture of the carrier solution and the acid can be converted, by means of adding a suitable alkaline compound to the aqueous mixture, into an alkaline salt solution which is pharmaceutically acceptable and therapeutically useful, when administered in a therapeutically effective quantity, in treating cancerous neoplasms which are susceptible to such treatment.

6. An injectable alkaline salt solution comprising: (a) an aqueous carrier solution which is pharmaceutically acceptable when injected into a mammalian patient, (b) an acid which is water-soluble and which has a molecular structure selected from the group consisting of:

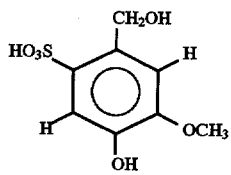

and salts and isomers thereof, and (c) a suitable alkaline compound at a concentration which elevates the pH of the alkaline salt solution to a level at least about 7.2, wherein the alkaline salt solution is pharmaceutically acceptable when injected and is therapeutically useful, when administered in a therapeutically effective quantity, in treating cancerous neoplasms which are susceptible to such treatment.

* * * * *